(12) United States Patent
Nelson

(10) Patent No.: US 12,370,293 B2
(45) Date of Patent: Jul. 29, 2025

(54) SYSTEM AND METHOD FOR BREAST PUMP FLANGE SIZING

(71) Applicant: Crystal Nelson, Redmond, OR (US)

(72) Inventor: Crystal Nelson, Redmond, OR (US)

( * ) Notice: Subject to any disclaimer, the term of this patent is extended or adjusted under 35 U.S.C. 154(b) by 828 days.

(21) Appl. No.: 17/679,979

(22) Filed: Feb. 24, 2022

(65) Prior Publication Data

US 2022/0265908 A1 Aug. 25, 2022

Related U.S. Application Data

(60) Provisional application No. 63/153,052, filed on Feb. 24, 2021.

(51) Int. Cl.
*A61M 1/06* (2006.01)

(52) U.S. Cl.
CPC ......... *A61M 1/064* (2014.02); *A61M 2207/00* (2013.01)

(58) Field of Classification Search
CPC ........ A61M 1/06; A61M 1/062; A61M 1/064; A61M 1/066; A61M 1/067; A61M 1/068; A61M 1/069; A61M 1/0693; A61M 1/06935; A61M 1/0697
See application file for complete search history.

(56) References Cited

U.S. PATENT DOCUMENTS

| | | | | |
|---|---|---|---|---|
| 6,387,072 | B1 * | 5/2002 | Larsson ................ | A61M 1/064 604/74 |
| 6,579,258 | B1 * | 6/2003 | Atkin .................... | A61M 1/066 604/74 |
| 2004/0181187 | A1 * | 9/2004 | Warburton ............ | A61M 1/066 604/74 |
| 2020/0405925 | A1 * | 12/2020 | Koster .................. | A61M 1/064 |
| 2022/0378989 | A1 * | 12/2022 | Quackenbush ....... | A61M 1/064 |
| 2024/0009361 | A1 * | 1/2024 | Bourquin ............. | A61M 1/0693 |

* cited by examiner

*Primary Examiner* — Dung T Ulsh
(74) *Attorney, Agent, or Firm* — Donn K. Harms

(57) ABSTRACT

A method for a system provider in a communication with a user over a computer network, allowing a determination of an optimum dimensioned breast flange for employment by the user with a breast pump. The identification of a model identifier of a flange which is best dimensioned for the physical characteristics of the breast of the user is determined from measurements taken and provided by the user remotely.

8 Claims, 5 Drawing Sheets

SYSTEM AND METHOD FOR BREAST PUMP FLANGE SIZING

FIELD OF THE INVENTION

This application claims priority to U.S. Provisional Patent Application Ser. No. 63/153,052 filed on Feb. 24, 2021, which is incorporated herein in its entirety by this reference thereto.

The present application relates to breast feeding of infants by their mothers. More particularly, it relates to a device and method enabling mothers to accurately determine the proper flange size of flange for comfortable employment with their breast pump.

BACKGROUND OF THE INVENTION

Throughout the world, and for millennia, breast feeding has been a primary source of nutrition for infants. Breast feeding as is conventionally well known, is the process of feeding breast milk by the mother, to her infant. This process can either be accomplished directly from the breast of the mother, or alternatively, by expressing milk from the breast and then bottle-feeding the expressed breast milk to the infant.

Most medical authorities recommend that an infant begin breast feeding within a few hours of birth and to allow the infant to consume as much as the infant desires. During the first few weeks after their birth babies may nurse roughly every two to three hours or more. The duration of such nursing sessions is generally a ten to fifteen minute duration on each breast of the mother.

Where the schedule of the mother or infant does not allow such constant feeding sessions, it is common for mothers to employ a pumping device to express breast milk and then store it for subsequent feedings. Conventionally, such sessions for expressing breast milk employ a flange which sealably engages with the breast of choice. A pump is operatively attached to the flange to thereby express milk to a container for storage and later use for feeding sessions.

When employing a breast pump to express milk for subsequent feedings, a very important consideration for both comfort and maximizing expressed milk is the size of the pump flange being employed. A breast pump flange of a proper size should fit comfortably around the nipple of the breast prior to and during pumping by the engaged breast pump.

During time periods where a breast pump is communicating suction to the flange, the nipple should not be touching the interior flange prior to pumping. However, the nipple will subsequently contact against the interior cavity of the cone shaped flange once pumping is started. This is due to normal swelling and suction caused by pumping.

Such a proper fitting insures that there is no discomfort to the mother which will negatively impact both the duration and amount of milk output. Further, a comfortably fitting flange will insure that when the mother later breast feeds the infant directly, that there is no tenderness or other discomfort.

The forgoing description concerning breast feeding and breast pumps is intended to be illustrative and not exclusive. As such, no limitations on the invention described and claimed herein is to be associated with such. Further, additional limitations and features of the current art of breast pumps are well known, or such will become apparent to those skilled in the art upon a reading and understanding of the specification below and the accompanying drawings.

SUMMARY OF THE INVENTION

The system and method herein in various modes provides a flange device and a method yielding significantly improved measurements for the proper and comfortable sizing of breast pump flanges to the breast of a mother using such breast pumps. The system, through the provision and employment of remotely configurable measuring gauges or components, is communicable over a computer network, such as the internet. Such provides users, such as mothers, the ability to easily configure and then use a breast measuring device to accurately and properly match her breast configurations to the proper sized breast pump flange. The measuring device may also be preassembled and sent to users vial mail or other modes of shipment in a slower system.

In a simple mode of the system and device herein, in a first step, directions are provided to a user on how to measure the diameter of the nipple of their breast using a measuring device in the form of gauge from a component with a known diameter.

By gauge or measuring component with a known diameter herein is meant one or more of widely available household items wherein there is an industry standard or government determined standard for dimensions thereof. The system provider, by compiling data upon the industry standard dimensions of the round side or end of such household items, will allow the user to employ one to ascertain a proper sized breast flange.

Alternatively the measuring component may be a printable gauge which will provide the desired measurement of the exterior surface of the nipple of a breast. Such a printable gauge may be communicated from the system provider to users over a computer network from the system provider computer to that of each user. The printable gauge can be sent as a conventional computer file such as a jpeg file or PDF file, wherein the user may print the page having a rendering of the gauge thereon.

In all modes of such measuring and comparing in the system herein, the interior diameter or size of currently sold and available breast pump flanges are gathered into a flange size database wherein the diameter of an interior cavity which is to be positioned over the nipple of the breast of each is ascertained and associated with the model identifier of the flange. By model identifier is meant the model name and/or product number assigned to each such flange by the manufacturer or distributor thereof, which the user may purchase or already have.

In the system, where a commonly available component, having industry standard dimensions is employed for a gauge, for example, the diameter of a common AA battery and/or the diameter of a coin, such as a penny or dime, the diameter of the round area of such is compared with the diameter of the nipple of the breast of the user. When a diameter closest to matching the diameter of the nipple of the user is ascertained as a determined breast measurement, such is communicated to the system provider. The determined breast measurement associated to the nipple of the user and communicated to the system provider, is cross referenced with individual available flanges having interior diameters to determine a match. An additional length may be added to the determined measurement for comfort.

In operation of the system herein, in this step, the user is provided instructions on measuring a size of the diameter of their breast nipple, through comparison thereof to the diameter of an object having a known standard dimension, such as AA battery or a coin or other gauge or measuring component with a known diameter.

Once the user determines a match to a comparison size of their nipple to that of the battery or coin or other component identified with a known diameter in one dimension, the system employing a computer having software running in memory operating to the task of reviewing a look-up table of flanges having interior cavities will operate to identify one or more flanges having an interior diameter matched to the determined nipple diameter. In a match to the measurement of their breast nipple discerned in the lookup, the user is then provided with the identification of a brand, or type, or place to purchase one or more available choices of breast flanges identified to match their communicated measurement to allow them to purchase or use it.

In another mode of the system herein which provides significantly improved accuracy as to matching a breast flange size to that of the nipple of the user, a remotely printable gauge or measuring component is communicated to the user over a network connection. The printable measuring device can be printed locally by the user. Once printed, it may be cut out of paper and assembled to form a measuring device. This assembled measuring gauge is then employed as the measuring component by the remote user to more accurately measure the nipple diameter of the breast of the intended user.

Higher accuracy of both the measurement and the accuracy of the size of the measuring device to be cut out by the user, is provided by a dimensional accuracy check of their printer in printing the gauge. This dimensional accuracy check or determinator may be remotely printed concurrently with the measurement tool to be cut out from the paper.

Prior to cutting out the printed tool components for assembly of a gauge, the user is provided with a printed circle which correlates to the dimensions of the printable gauge or measuring component. The user will be directed to compare the diameter of one or more printed circles on the page printed by their printer to a coin diameter, such as a penny. If the diameter of the printed circle matches the diameter of the coin with a known diameter, such as a penny, the user is provided assurance that the printed gauge or measuring components will be properly sized. This sizing step was found to provide assurance that the printer of the user is printing the gauge or measuring component in the proper dimensions to yield accurate measurements. By matching the size or diameter of the printed circle, which is printed on the same sheet of printable material as the gauge to be cutout, the user is, thus, assured the printed measuring device will yield accurate measurements of the nipple of the breast of the user.

Once the nipple diameter size is determined using the measuring device, as with other steps in the system herein, it may be cross referenced to a the predetermined measurements held in database of breast pump flanges. A match between the determined nipple size and the interior diameter of a passage, in one or more of the flanges in the electronic database, will determine the proper sized breast flange which is a match to the measured diameter of the nipple.

Experimenting with numerous flanges over a duration of time has helped determine that a proper sized flange, from those in the database, will preferably be one which is sized to yield a small gap or space from the measured nipple exterior size to the interior wall of the passage in the flange. This gap or space is currently at least 1 mm circumferentially between the exterior of the circumference of the nipple to the interior surface of the flange. Thus, once the user employs the gauge or measuring tool herein and provides the accurate measurement of their nipple diameter, a diameter and/or circumference thereof can be calculated and such will result in a determination of a correct chosen flange, which will yield the desired space or gap, from the database thereof.

In all modes, where an existing assembled or assemblable measuring tool is provided to the user for measuring, it was found that when an object, such as a penny or battery with a known diameter is not used, a pair of L-shaped members worked best for a measuring tool for the user to operate and measure. This printable measuring tool may be cutout locally and has one L-shaped member which is engaged to translate through a formed aperture in the other L-shaped member.

While the original L-shaped members had intersecting perpendicular sides, it was unexpectedly found during experimentation that forming a curve on both L-shaped members on the contact surface thereof with opposite sides of the nipple, provided significantly improved results. Such was determined to occur due to the more comfortable contact against the skin of the user during use.

Once the unexpectedly enhanced outcome of the curved shape of both contact surfaces of the L-shaped members was determined to enhance results, the curves thereon were further experimented with and shaped such that they matched the interior curved surfaces of breast pump flanges correlating to the determined diameter of the measured breast. Thus, the mode of the system employing opposing curved surfaces of the engaged L-shaped members of the measuring tool is particularly preferred, as it yields a significantly more comfortable fit of the flange to the user, by mimicking the curved intersections of an axial passage of the breast flange with the angled wall portion of the flange.

In another mode of the device herein a breast nipple diameter gauge or measuring tool can be provided assembled or can be provided in the mode noted where the user can print it and cut it out and assemble it. In this mode, a window is provided in one of the L-shaped members for proper positioning of indicia of the measurement increments printed on a cross member extending from the other of the L-shaped members. The curved shape of both L-shaped members is also preferred in this mode to help match the interior curve of the correlating breast flange to the curve of the breast of the user.

Concerning the above disclosure, those skilled in the art will appreciate that the conception upon which this disclosure is based may readily be utilized as a basis for designing other breast flange sizing systems and for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. The term "substantially" when employed herein, means plus or minus twenty percent unless otherwise designated in range.

It is an object of the present invention to provide for an easy to use and understand system providing users an accurate measuring of the breast of nursing mothers to subsequently match and properly fit a breast flange.

It is a further object of this invention to provide such a measuring system which can be communicated over a network, such as the internet, to the computing device of a mother or other individual.

It is a further object of this invention to provide such a breast measuring system and device where the device is printed and cut out remotely and where the proper sizing of the cut out device is determinable by the user using a provided size confirmation system.

A further object of this invention is the provision of opposing curved surfaces on the measuring device, which correlate to the curve of the interior sidewall of a breast pump flange at the intersection of a frusto conical portion thereof with a linear portion.

These and other objects, features, and advantages of the presently disclosed breast measurement system and device to properly size breast flanges, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive examples of embodiments and/or features of the disclosed pipe engageable liquid containment device. It is intended that the embodiments and figures disclosed herein are to be considered illustrative of the invention herein, rather than limiting in any fashion.
In the drawings.

DETAILED DESCRIPTION OF THE INVENTION

Figure 1:
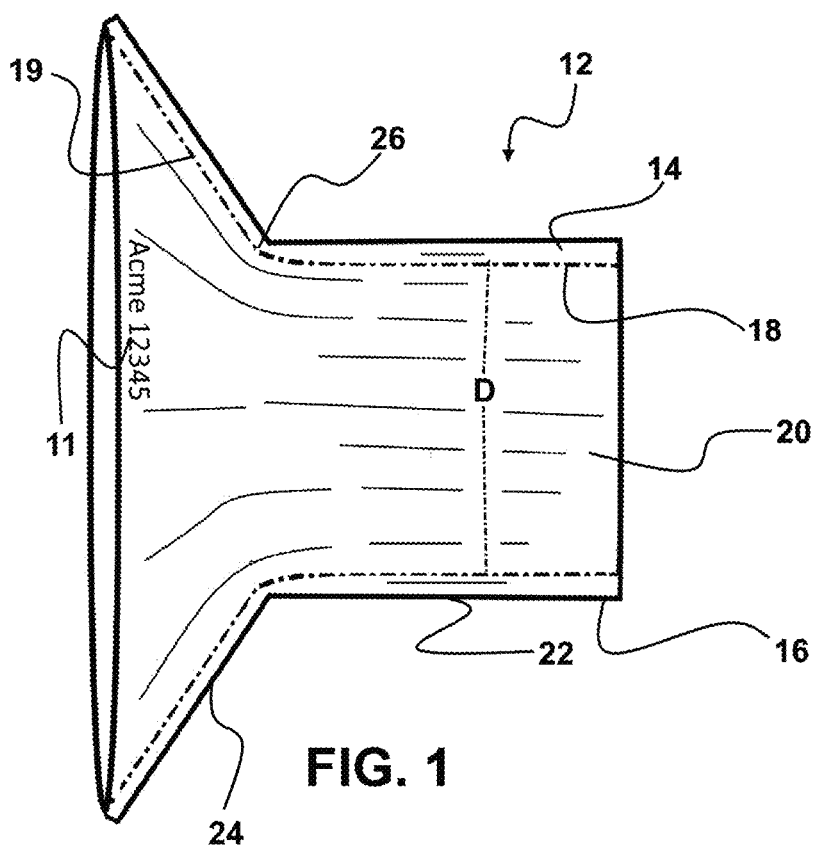
FIG. 1 depicts a sectional view through a widely provided and sold conventional breast pump flange showing an interior passage having a linear portion and an intersection thereof with a frusto conical portion of the interior passage and sidewall.

In this description, the directional prepositions of up, upwardly, down, downwardly, front, back, top, upper, bottom, lower, left, right, front, back, and other such terms refer to the device as it is oriented and appears in the drawings and are used for convenience only and such are not intended to be limiting in any fashion, or to imply that the device has to be used or positioned in any particular orientation. Where steps are defined in a method, the steps may be reordered.

Now referring to drawings in FIGS. 1-8 wherein similar components are identified by like reference numerals, there is seen in FIG. 1 a breast pump flange 12 each of which would be associated with a model identifier 11 and correlated to a respective flange size in the flange size database.

Figure 2:
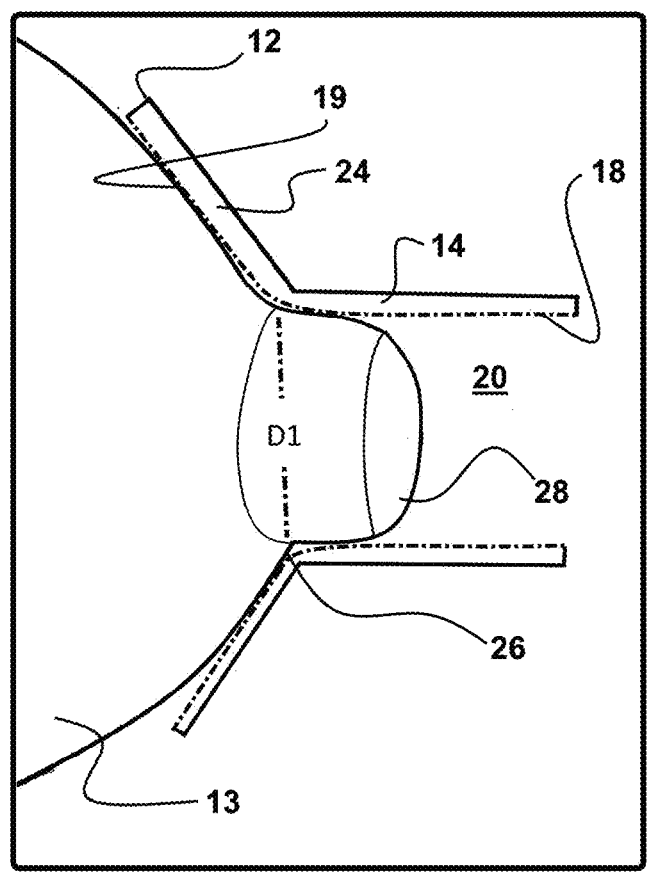
FIG. 2 shows a sectional view of the breast pump flange of FIG. 1, operatively positioned upon a breast and showing opposing curves of the surface of the interior sidewall of the flange at an intersection between the cone or conical portion with a linear portion thereof.

As shown, each such flange, by design, is adapted to engage with a breast 13 of the user, as in FIG. 2, and a breast pump device (commonly known but now shown) during a pumping session to express breast milk. As shown in the sectional view, each such flange 12 has a sidewall 14 which has an exterior surface 16 opposite an interior surface 18. The interior surface 18 surrounds and defines a diameter D and circumference of the interior cavity 20 of the flange 12.

The flange 12 has a linear portion 22 which is adapted to engage with a breast pump on one end which is opposite a cone shaped or frusto conical portion 24 of the flange 12 which is configured to removably contact against the breast 14 of the user surrounding the nipple thereof. At an intersection of the interior cavity of the linear portion 22 and the frusto conical portion 24, a curved surface 26 portion is formed. As can be seen, this curved surface 26 portion is formed where the interior surface 18 curves from a straight or linear configuration along the interior cavity 20 of the linear portion 22 of the flange 12, to form the secondary interior surface 19 of the frusto conical portion 24 of the flange 12. While this curved surface 26 has conventionally not been deemed as important, during experimentation herein, it was found that the angle of this curved surface 26 had a significant effect on the comfort of the user.

As shown in FIG. 1 and FIG. 2, the interior cavity 20 of the linear portion 22 of the flange 12 has a diameter "D" extending between the interior surface 18 defining the size and diameter of the linear interior cavity 20. In all modes of the device and system herein, the diameter D of the respective interior cavity of each flange 12 is stored in the flange size database or in a lookup table or a database of individual flanges 12. Once the diameter of the nipple D1 is determined for each flange 12 it may be correlated and matched to a measured diameter D of each respective flange 12 by the model identifier in the database to ascertain a match to a commercially available flange 12.

In a simple mode of the system herein, this lookup of the flange 12 by model identifier and a match of its diameter D to that measured by the user, can be done manually. However, using software running in memory on a network connected computer which is operating to the task of matching the user measured nipple diameter D1 to (FIG. 3) the known diameter D of one or more model-identified flanges 12, allows for remote use by users over a computer network, such as the Internet. In this matching of the measured breast diameter D1 communicated from a user to flange diameter D of a model identifier of a commercially available flange, the identification of a properly sized and most comfortable flange 12 can be provided to a user based on their measurement of the nipple 28 taken remotely.

Also shown in FIG. 2, the curved surface 26 of the interior of the flange 12 is also preferred as it helps to substantially match the curve of the breast 13 of the user at a point between the nipple 28 and the surrounding breast tissue area. Most commercially available flanges 12 have such a curved surface 26. However, such has not been accommodated in the measuring of the nipple by the user.

Figure 3:
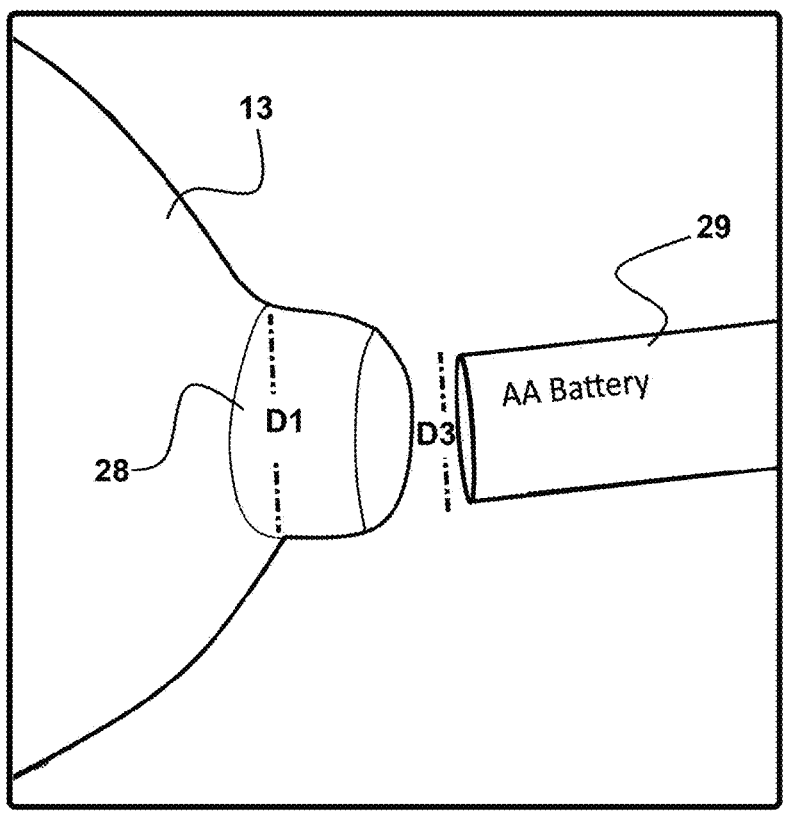
FIG. 3 depicts the employment of a gauge or measuring tool which is a battery having a commonly know diameter to compare and ascertain a nipple diameter.

Shown in FIG. 3 is a depiction of a user employment of a gauge or measuring tool which is has an industry standard size for at least one circular portion. For example, coins have a government dictated diameter and objects, such as a common battery, have a known battery 29 diameter D. Such batteries come in different sizes and the length and diameters thereof are industry standard and the circular diameter is known as they must fit within conventional battery compartments. Using a battery 29 as the gauge or measuring tool, the user compares it with the nipple diameter D1 to ascertain a match thereof or a mismatch, where one of the two is smaller or larger.

Where a match is determined and communicated from the user, a match to a proper sized flange 12 can be determined. To determine a match from a table or flange size database of flanges 12 known to have a diameter D, which best matches the diameter D3 of the battery, the measured diameter is compared to that of those in the flange size database, and a properly dimensioned flange 12 is ascertained and provided to the user. This may be done, as noted above, using software running in memory on computer which may be engaged to a network, which operates to the task of receiving a measured diameter size from the user, and correlating such to the model identifiers in the flange size database to determine a match of D to D1. This would be the process for all nipple measurements provided by the user to the system provider, no matter the tool or object used for the measurement.

Figure 4:
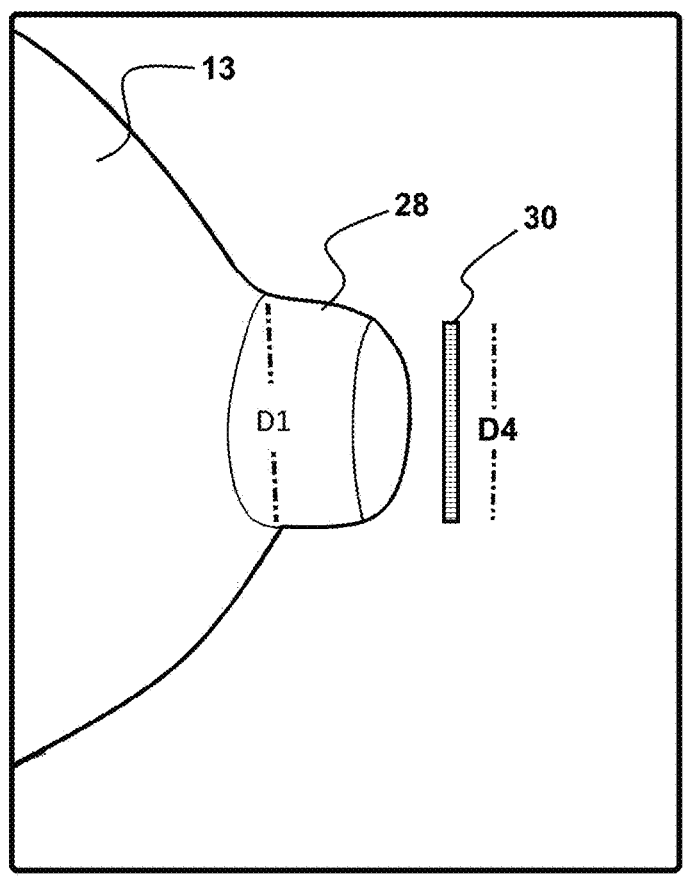
FIG. 4 shows the employment of a gauge or measuring tool in the configuration of a coin, having a known coin diameter to compare and determine a nipple diameter.

As shown in FIG. 4, the user may also employ, as directed, a coin 30 as the gauge or measuring tool. Coins 30 conventionally have a known diameter D4. To determine the properly sized flange 12, the coin diameter is used to measure and determine if a match is present between the coin 30 diameter D4 and the nipple diameter D1. A match is determined of the nipple diameter D1 with the coin diameter D4 from the table or flange size database of available flanges 12, where at least one flange 12 by model identifier, in the flange size database, has a diameter D thereof, which best substantially matches the diameter D4 of coin 30. Since there are multiple conventional coins 30 with each having a known diameter, a match can be ascertained between the diameter D4 of the identified coin used and identified by the user (penny, dime, nickle) and the best matching flange 12 diameter D. The identified matching flange 12 can then be provided to the user.

The user, in using objects such as a coin or battery, need not communicate the matching circular surface diameter but only what object was used. Software running in the electronic memory, operating to the task of looking up the diameter measurement in a database of objects having known diameters, will ascertain a diameter measurement by matching the identified object to the known diameter thereof.

Figure 5:
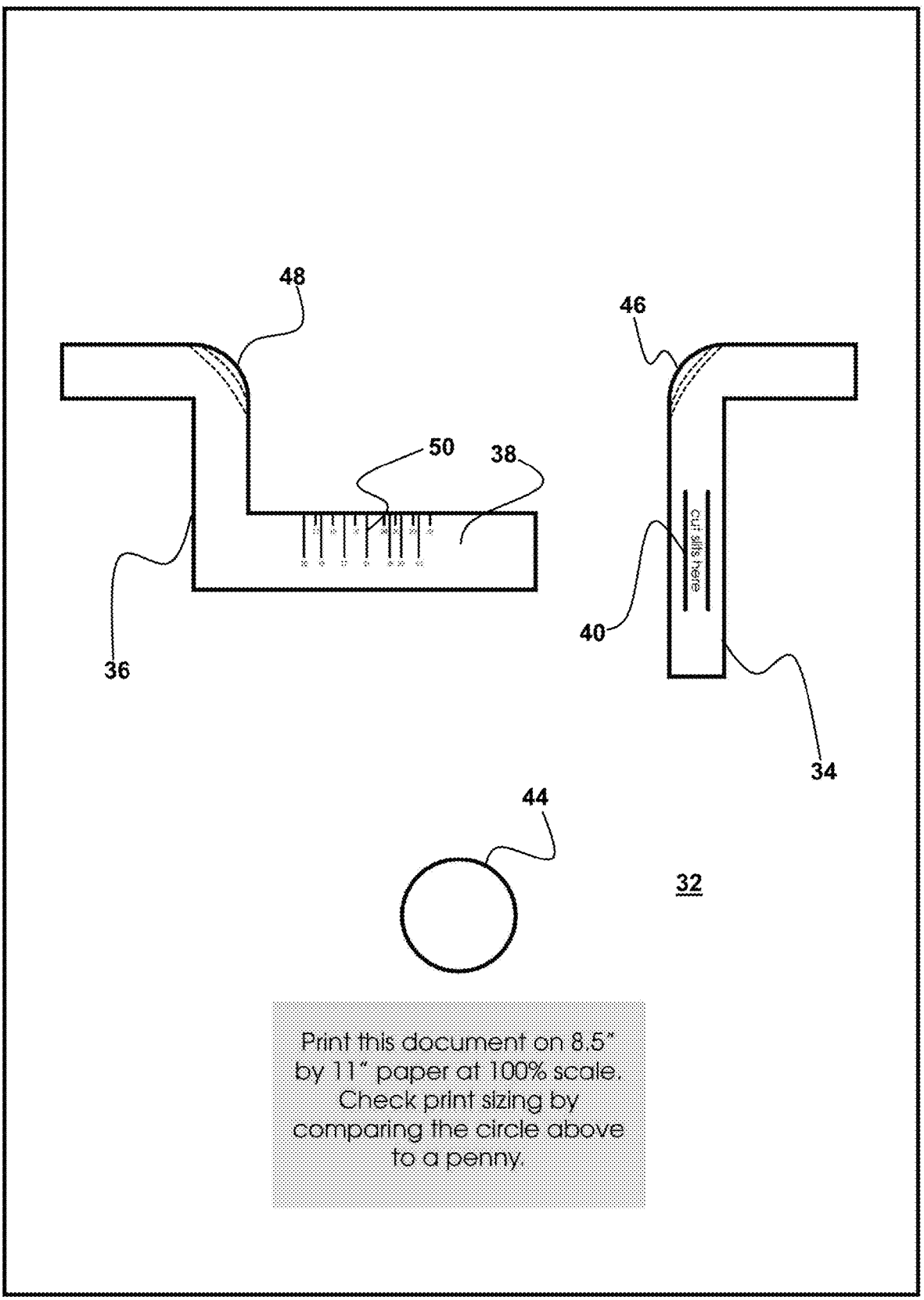
FIG. 5 depicts a printed page which may be communicated to the remote computing device of the user and printed and shows two L-shaped assemblable members forming the gauge or measuring tool and a circle which is employable to validate the correct printed size of the printed L-shaped members.
Figure 6:
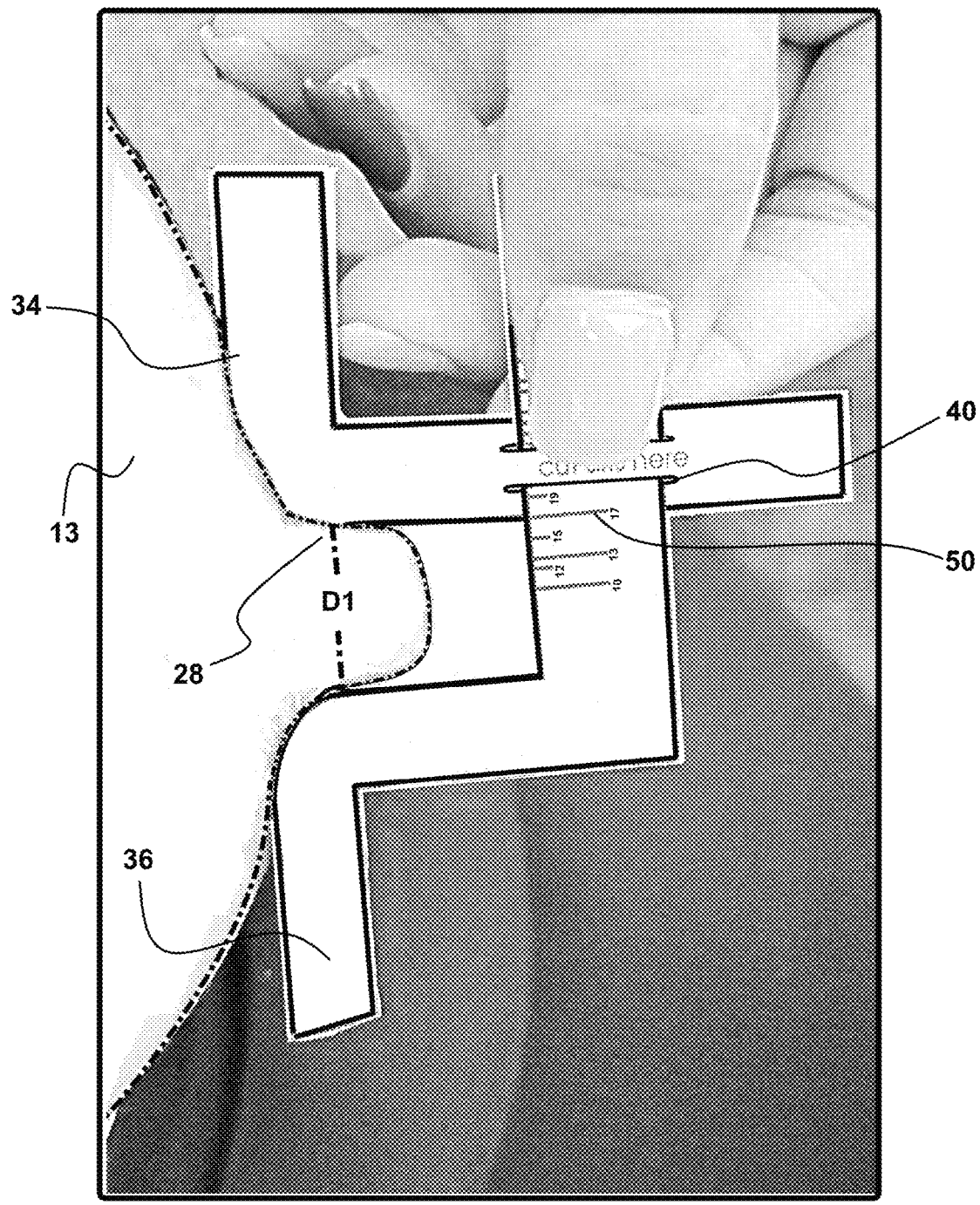
FIG. 6 depicts the assembled gauge or measuring tool of FIG. 5 or 7 in operative engagement to measure the nipple diameter of a breast, and showing the opposing curved surfaces of the gauge formed of L shaped members in contact with the curved surface of the breast.
Figure 7:
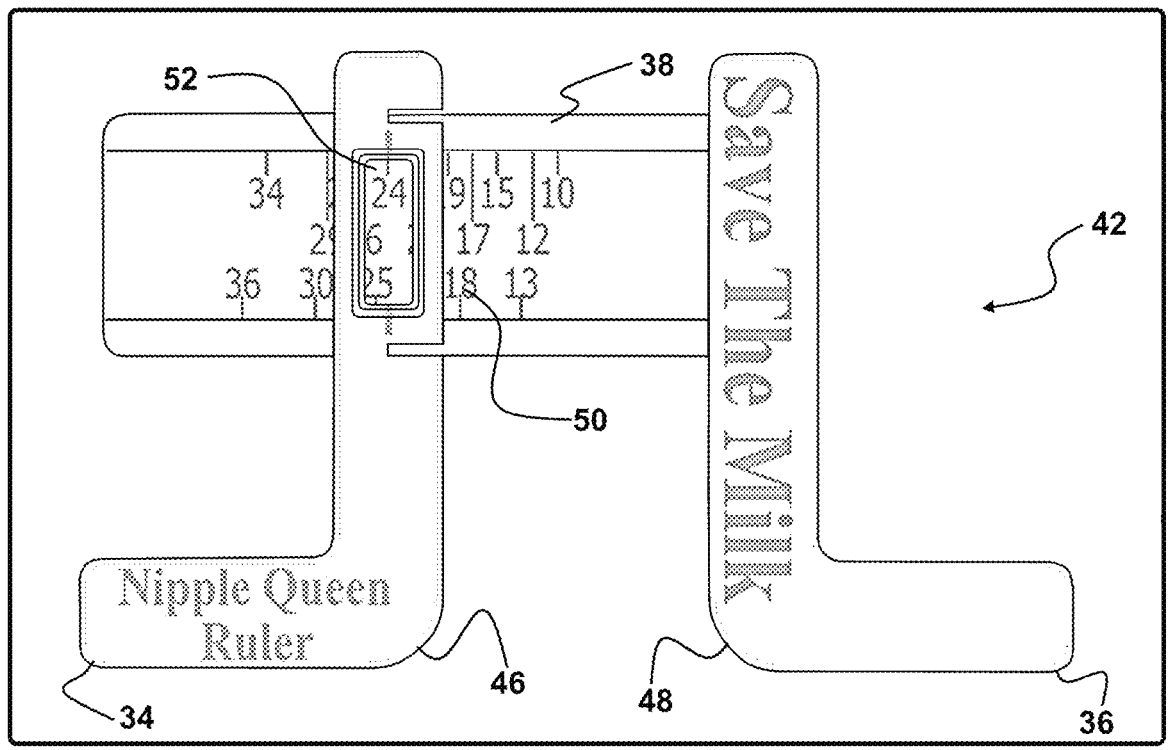
FIG. 7 shows another mode of the measuring tool device herein which can be provided assembled and ready to use or can be provided in a printable page as in FIG. 5, to allow the user to cut it out and assemble it, where a window is also provided to aid in measurement reading.

Shown in FIG. 5 is an especially preferred mode of the system. Shown is a printed page 32 which may be communicated to the computing device of the user over a network for printing locally to cut out and assemble a caliper as a gauge. As shown, there is a first L-shaped member 34 and a second L-shaped member 36. Also shown is a measuring member 38 which extends from the second L-shaped member 36. This measuring member 38 is engageable through one or a plurality of slits 40 the user is instructed to cut to communicate through the body of the first L-shaped member 34 to form a nipple diameter gauge or measuring tool 42 such as shown in FIGS. 6 and 7.

Additionally shown, printed on the page 32 in FIG. 5 is a printing dimension correctness determinator 44. A diameter of the dimension correctness determinator 44 is compared by the user with a known diameter of a coin or the like to determine a match thereof or mismatch. To test the correctness of the printer, a match between the diameter of the employed coin, such as a penny or dime or other object such as a battery, and the diameter of the dimension correctness determinator 44 should be found. This is done by placing the coin or object such as a battery within the dimension correctness determinator 44. Where the two match, the user is provided a visual cue that the printed gauge in the form of the caliper measurement tool 42 formed of the L-shaped members are dimensioned correctly in the printing and will yield accurate measurements.

Also shown and preferred, for more accurate measurements, are a first curved edge 46 positioned on the first L-shaped member 34 and a second curved edge 48 located on the second L-shaped member 36 forming the caliper. The curves size and shape may be varied by providing printed dotted cutting lines for the user to change the shape of the curves 46 and 48. The user, during measurement of the breast as in FIG. 6, can ascertain if the curves 46 and 48 being used are the most comfortable or may change the curves 46 and 48 shape to those depicted in dotted line to find the most comfortable curved edge shape.

Once the best curve is determined and once the diameter D1 of the nipple is determined by the matching measurement indicia 50, such as the line positioned closest to or adjacent the slit 40, software running in memory of the computer of the system provider can employ that diameter to calculate a circumference of the nipple of the user.

In another optional but preferred step in the method herein, using this calculated circumference of the nipple of the user, between 0.5-2 mm is added to the calculated circumference from the measured diameter D1 matching the measurement indicia 50. The diameter of a flange 12 having a model identifier which has a diameter yielding the calculated circumference which is slightly large can be ascertained by software operating to that task. Thereafter, the model identifier of the fitting flange 12 matching the anatomy of the user including the larger calculated circumference, can be determined and provided.

It should be noted that the indicia 50 positioned on all of the caliper type gauges or measuring tools 42 herein, may not provide the actual measurements in the typical 1-10 mm. Instead, in another mode, it may provide the user with the model identifier of the nipple 14 best suited to fit them, which can be discerned where the indicia 50 is positioned to yield a diameter which adds 0.5-2 mm to the actual diameter of the nipple. Consequently, in a mode wherein the system provider need not make the calculation of actual nipple measurements, the indicia 50 as placed herein, rather than an actual measurement such as from 1-10 mm on a normal ruler, would have a readable result of a measurement using the indicia 50 as printed is actually 3-12 mm. This will result in the choosing from the flange size database of a model identifier of a flange 12 which has a 0.5-2 mm clearance. In some case, the user may also choose a model identifier of a flange 12 they may already have, which matches the larger measurement when measured with a ruler by the user, and prevents calculation errors.

As noted above, when the actual diameter size is used, the system determines the flange identifier of the correct flange 12 using the flange size database with known circumferential measurements by changing the math of the calculation based on the user provided actual measurements. This will allow for the determination of the flange identifier of the flange 12 having the substantially 0.5-2 mm gap circumferentially around the nipple prior to use.

Shown in FIG. 7 is another mode of the caliper type gauge or measuring tool 42 herein which operates substantially the same as that of FIG. 6. In this mode, it can be provided assembled and ready to use or can be provided in a printable page 32, as in FIG. 5, to allow the user to cut it out and assemble it. As shown, the gauge or tool 42, as in FIG. 7, operates the same as that of FIG. 5-6 but also includes a measurement window 52 for more accurate measuring of measurement indicia 50 which is located within the window 52 during nipple diameter D1 measurement. Curves 46 and 48, as with the mode in FIG. 5, can also be provided with multiple curved shapes or dotted lines for cutting such to allow the user to ascertain the most comfortable curves 46 and 48 to cross reference during fitment.

Figure 8:
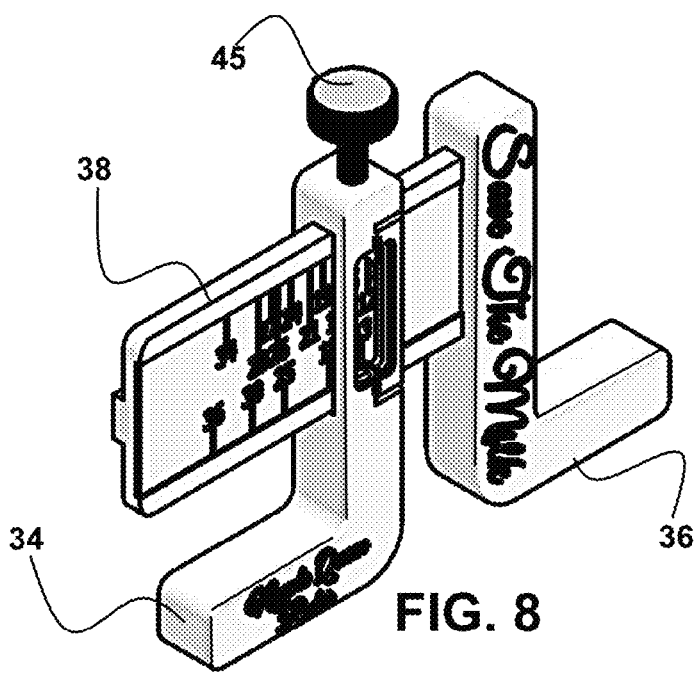
FIG. 8 is a perspective view of a mode of the device as in FIG. 7, which includes a position fixing component or lock, to hold the components in place once removed from the breast.

In FIG. 8 is shown a perspective view of a mode of the measuring tool device as in FIG. 7. This mode of the device includes a position fixing member 45, such as a set screw, to hold the two engaged L-shaped members in place once removed from the breast. This mode will avoid any slippage and mis-measurement, once the device is removed from the breast.

It should be noted in all modes of the system herein that the system provider, in a final step, can sell the user the flange having the model identifier, which is determined as above, to most comfortably and correctly fit their breast. This is particularly preferred in service users who may not live proximate to stores having the identified flange.

In a synopsis of the above noted steps of method of employment of the system herein in a first step the user employs a measuring tool to determine an actual diameter of the nipple of their breast and communicates that actual diameter to the system provider.

The system provider, from an amassed flange size database, which has the diameters of the interior cavity to be positioned over the nipple, correlates the communicated actual diameter provided and matches it to a model identifier of a flange in the flange size database to determine a matching model identifier of at least one flange in the flange size database.

The matching model identifier of the flange determined most comfortable for the user, is communicated to the user.

Optionally, the system provider can, in another step, sell a flange to the user having the matching model identifier.

In another step, that is preferred, an actual circumference of the nipple is calculated using the actual diameter communicated above and determines the model identifier of a flange which is 0.5 to 2 mm larger than the actual circumference In another step, which is preferred for accuracy, the measuring tool is communicated over a network to the user in the form of a gauge, which may be cut from a printed page, whereafter the user will measure their nipple.

In another optional, but preferred step for more accuracy, the communicated printed page has a measuring tool in the form of an assemblable caliper.

In another optional but preferred step in the system, a dimension correctness determinator is included on the printed page and the user matches the diameter thereof to a diameter of an object having a known diameter matching the diameter of the dimension correctness determinator.

It should be noted that any of the different depicted and described configurations and components of the breast flange size determination system herein, can be employed with any other configuration or component shown and described as part of the device herein. Additionally, while the present invention has been described herein with reference to particular embodiments thereof and/or steps in the method of production or use, a latitude of modifications, various changes and substitutions are intended in the foregoing disclosure, and it will be appreciated that in some instance some features, or configurations, of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A method for a system provider in a communication with a user over a computer network to determine and communicate to said user a breast pump flange for positioning between the breast of a user and a breast pump, comprising:

having said user employ a measuring tool to measure an actual diameter of a nipple of their breast;

having said user communicate said actual diameter to said system provider;

determining a matching product identifier of an individual breast pump flange by comparing said actual diameter communicated from said user to the respective known diameters of a nipple-engaging passage associated with each respective breast pump flange in a database of breast pump flanges having respective product identifiers associated therewith; and communicating said matching product identifier to said user, whereby said user can procure a breast pump flange having said product identifier.

2. The method of claim 1, additionally comprising:

communicating to said user the identification of one or a plurality of objects where each of which have a known diameter to said system provider, of a circular side thereof;

having said user employ one of said plurality of objects as said measuring tool to match said diameter of said circular side thereof to a diameter of their nipple;

in providing said actual diameter, having said user identify to said system provider, the specific object employed which had a said circular side matching the diameter of their nipple; and determining said actual diameter of the nipple of said user from said known diameter of said circular side of said specific object employed.

3. The method of claim 1, additionally comprising:

communicating to said user a printable page having said measuring tool thereon, which may be cut therefrom.

4. The method of claim 3, additionally comprising:

positioning a dimension correctness determinator upon said printable page; and having said user employ an object having a circular side identified as matching a diameter of said dimension correctness determinator to confirm a match therebetween as an indicator the dimensions of said measuring tool are correct.

5. The method of claim 1, additionally comprising:

calculating an actual circumference of said nipple of said user from said actual diameter;

adding 0.5 to 2 mm to said actual circumference;

employing said actual circumference to determine a secondary diameter; and substituting said secondary diameter for said actual diameter in the step of determining said matching product identifier which is subsequently communicated to said user.

6. The method of claim 2, additionally comprising:

calculating an actual circumference of said nipple of said user from said actual diameter;

adding 0.5 to 2 mm to said actual circumference;

employing said actual circumference to determine a secondary diameter; and substituting said secondary diameter for said actual diameter in the step of determining said matching product identifier which is subsequently communicated to said user.

7. The method of claim 3, additionally comprising:

calculating an actual circumference of said nipple of said user from said actual diameter;

adding 0.5 to 2 mm to said actual circumference;

employing said actual circumference to determine a secondary diameter; and substituting said secondary diameter for said actual diameter in the step of determining said matching product identifier which is subsequently communicated to said user.

8. The method of claim 4, additionally comprising:

calculating an actual circumference of said nipple of said user from said actual diameter;

adding 0.5 to 2 mm to said actual circumference;

employing said actual circumference to determine a secondary diameter; and substituting said secondary diameter for said actual diameter in the step of determining said matching product identifier which is subsequently communicated to said user.

\* \* \* \* \*